United States Patent
Houchins et al.

(10) Patent No.: US 6,262,244 B1
(45) Date of Patent: Jul. 17, 2001

(54) DNA AND AMINO ACID SEQUENCE SPECIFIC FOR NATURAL KILLER CELLS

(75) Inventors: Jeffrey P. Houchins, Lino Lakes, MN (US); Toshio Yabe, Chiba (JP); Cynthia M. McSherry, Maple Grove, MN (US); Fritz H. Bach, Manchester, MA (US); Erhard Hofer, Vienna (AT)

(73) Assignees: Regents of the University of Minnesota, Minneapolis, MN (US); Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/543,246

(22) Filed: Oct. 13, 1995

Related U.S. Application Data

(63) Continuation of application No. 08/122,514, filed as application No. PCT/US92/02469 on Mar. 27, 1992, now abandoned, which is a continuation-in-part of application No. 07/676,663, filed on Mar. 28, 1991, now abandoned.

(51) Int. Cl.$^7$ .......................... C07H 17/00; C07K 14/00
(52) U.S. Cl. .................................. 536/23.5; 514/2; 514/8; 530/350
(58) Field of Search .................................. 536/23.1, 23.5; 514/2, 8; 530/350; 435/69.7, 69.1

*Primary Examiner*—Karen Cochrane Carlson
(74) *Attorney, Agent, or Firm*—Melvyn M. Kassenoff

(57) ABSTRACT

Proteins expressed in NK and some T cells and being transmembrane molecules with Type II membrane protein structure, the extracellular part of the receptor being characterized by a C-type animal lectin domain, DNA sequences encoding such proteins and antibodies against the extracellular part of the transmembrane protein which can activate NK and T cells.

16 Claims, 1 Drawing Sheet

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
        (A) LENGTH: 1387 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (ix) FEATURE:
         (A) NAME/KEY: CDS
         (B) LOCATION:165..863

(xi) SEQUENCE DESCRIPTION: SEQ ID NO: 1:

```
GCAGGCATTG TTTGTTCTTG TCTTGGATTT ATGCCTTTAA ATTTCACCTT TTATTACACA      60

GCTATAGCAG GCCTTTTTAT GAGACTAACC TGGCCTCTCC ACTAAAGGAT GTGTGACTTT     120

CTGGGGACAG AAGAGTACAG TCCCTGACAT CACACACTGC AGAG ATG GAT AAC CAA     176
                                              Met Asp Asn Gln
                                                1

GGA GTA ATC TAC TCA GAC CTG AAT CTG CCC CCA AAC CCA AAG AGG CAG      224
Gly Val Ile Tyr Ser Asp Leu Asn Leu Pro Pro Asn Pro Lys Arg Gln
  5              10                  15                  20

CAA CGA AAA CCT AAA GGC AAT AAA AGC TCC ATT TTA GCA ACT GAA CAG      272
Gln Arg Lys Pro Lys Gly Asn Lys Ser Ser Ile Leu Ala Thr Glu Gln
              25                  30                  35

GAA ATA ACC TAT GCG GAA TTA AAC CTT CAA AAA GCT TCT CAG GAT TTT      320
Glu Ile Thr Tyr Ala Glu Leu Asn Leu Gln Lys Ala Ser Gln Asp Phe
          40                  45                  50

CAA GGG AAT GAC AAA ACC TAT CAC TGC AAA GAT TTA CCA TCA GCT CCA      368
Gln Gly Asn Asp Lys Thr Tyr His Cys Lys Asp Leu Pro Ser Ala Pro
      55                  60                  65

GAG AAG CTC ATT GTT GGG ATC CTG GGA ATT ATC TGT CTT ATC TTA ATG      416
Glu Lys Leu Ile Val Gly Ile Leu Gly Ile Ile Cys Leu Ile Leu Met
  70                  75                  80

GCC TCT GTG GTA ACG ATA GTT GTT ATT CCC TCT ACA TTA ATA CAG AGG      464
Ala Ser Val Val Thr Ile Val Val Ile Pro Ser Thr Leu Ile Gln Arg
 85                  90                  95                 100

CAC AAC AAT TCT TCC CTG AAT ACA AGA ACT CAG AAA GCA CGT CAT TGT      512
His Asn Asn Ser Ser Leu Asn Thr Arg Thr Gln Lys Ala Arg His Cys
                105                 110                 115

GGC CAT TGT CCT GAG GAG TGG ATT ACA TAT TCC AAC AGT TGT TAC TAC      560
Gly His Cys Pro Glu Glu Trp Ile Thr Tyr Ser Asn Ser Cys Tyr Tyr
            120                 125                 130

ATT GGT AAG GAA AGA AGA ACT TGG GAA GAG AGT TTG CTG GCC TGT ACT      608
Ile Gly Lys Glu Arg Arg Thr Trp Glu Glu Ser Leu Leu Ala Cys Thr
        135                 140                 145

TCG AAG AAC TCC AGT CTG CTT TCT ATA GAT AAT GAA GAA GAA ATG AAA      656
Ser Lys Asn Ser Ser Leu Leu Ser Ile Asp Asn Glu Glu Glu Met Lys
    150                 155                 160

TTT CTG TCC ATC ATT TCA CCA TCC TCA TGG ATT GGT GTG TTT CGT AAC      704
Phe Leu Ser Ile Ile Ser Pro Ser Ser Trp Ile Gly Val Phe Arg Asn
165                 170                 175                 180

AGC AGT CAT CAT CCA TGG GTG ACA ATG AAT GGT TTG GCT TTC AAA CAT      752
Ser Ser His His Pro Trp Val Thr Met Asn Gly Leu Ala Phe Lys His
                    185                 190                 195

GAG ATA AAA GAC TCA GAT AAT GCT GAA CTT AAC TGT GCA GTG CTA CAA      800
Glu Ile Lys Asp Ser Asp Asn Ala Glu Leu Asn Cys Ala Val Leu Gln
                200                 205                 210

GTA AAT CGA CTT AAA TCA GCC CAG TGT GGA TCT TCA ATA ATA TAT CAT      848
Val Asn Arg Leu Lys Ser Ala Gln Cys Gly Ser Ser Ile Ile Tyr His
            215                 220                 225

TGT AAG CAT AAG CTT TAGAGGTAAA GCGTTTGCAT TTGCAGTGCA TCAGATAAAT      903
```

```
Cys Lys His Lys Leu
    230

TGTATATTTC TTAAAATAGA AATATATTAT GATTGCATAA ATCTTAAAAT GAATTATGTT      963

ATTTGCTCTA ATAAGAAAAT TCTAAATCAA TTATTGAAAC AGGATACACA CAATTACTAA     1023

AGTACAGACA TCCTAGCATT TGTGTCGGGC TCATTTTGCT CAACATGGTA TTTGTGGTTT     1083

TCAGCCTTTC TAAAAGTTGC ATGTTATGTG AGTCAGCTTA TAGGAAGTAC CAAGAACAGT     1143

CAAACCCATG GAGACAGAAA GTAGAATAGT GGTTGCCAAT GTCTGAGGGA GGTTGAAATA     1203

GGAGATGACC TCTAACTGAT AGAACGTTAC TTTGTGTCGT GATGAAAACT TTCTAAATTT     1263

CAGTAGTGGT GATGGTTGTA ACTCTGCGAA TATACTAAAC ATCATTGATT TTTAATCATT     1323

TTAAGTGCAT GAAATGTATG CTTTGTACAC GACACTTCAA TAAAGCTATC CAGAAAAAAA     1383

AAAA                                                                  1387

(2) INFORMATION FOR SEQ ID NO: 2:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Asn Gln Gly Val Ile Tyr Ser Asp Leu Asn Leu Pro Pro Asn
  1               5                  10                  15

Pro Lys Arg Gln Gln Arg Lys Pro Lys Gly Asn Lys Ser Ser Ile Leu
             20                  25                  30

Ala Thr Glu Gln Glu Ile Thr Tyr Ala Glu Leu Asn Leu Gln Lys Ala
         35                  40                  45

Ser Gln Asp Phe Gln Gly Asn Asp Lys Thr Tyr His Cys Lys Asp Leu
     50                  55                  60

Pro Ser Ala Pro Glu Lys Leu Ile Val Gly Ile Leu Gly Ile Ile Cys
 65                  70                  75                  80

Leu Ile Leu Met Ala Ser Val Val Thr Ile Val Val Ile Pro Ser Thr
                 85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ser Pro Ser Ser Trp Ile Gly
            165                 170                 175

Val Phe Arg Asn Ser Ser His His Pro Trp Val Thr Met Asn Gly Leu
                180                 185                 190

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
        210                 215                 220

Ile Ile Tyr His Cys Lys His Lys Leu
225                 230
```

(2) INFORMATION FOR SEQ ID NO: 3:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

```
CAGAGGCACA ACAATTCTTC CCTGAATACA AGAACTCAGA AAGCACGTCA TTGTGGCCAT      60
TGTCCTGAGG AGTGGATTAC ATATTCCAAC AGTTGTTACT ACATTGGTAA GGAAAGAAGA     120
ACTTGGGAAG AGAGTTTGCT GGCCTGTACT TCGAAGAACT CCAGTCTGCT TTCTATAGAT     180
AATGAAGAAG AAATGAAATT TCTGTCCATC ATTTCACCAT CCTCATGGAT TGGTGTGTTT     240
CGTAACAGCA GTCATCATCC ATGGGTGACA ATGAATGGTT TGGCTTTCAA ACATGAGATA     300
AAAGACTCAG ATAATGCTGA ACTTAACTGT GCAGTGCTAC AAGTAAATCG ACTTAAATCA     360
GCCCAGTGTG GATCTTCAAT AATATATCAT TGTAAGCATA AGCTT                    405
```

(2) INFORMATION FOR SEQ ID NO: 4:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 4:

```
CGTCATTGTG GCCATTGTCC TGAGGAGTGG ATTACATATT CCAACAGTTG TTACTACATT      60
GGTAAGGAAA GAAGAACTTG GGAAGAGAGT TTGCTGGCCT GTACTTCGAA GAACTCCAGT     120
CTGCTTTCTA TAGATAATGA AGAAGAAATG AAATTTCTGT CCATCATTTC ACCATCCTCA     180
TGGATTGGTG TGTTTCGTAA CAGCAGTCAT CATCCATGGG TGACAATGAA TGGTTTGGCT     240
TTCAAACATG AGATAAAAGA CTCAGATAAT GCTGAACTTA ACTGTGCAGT GCTACAAGTA     300
AATCGACTTA AATCAGCCCA GTGTGGATCT TCAATAATAT ATCATTGTAA GCATAAGCTT     360
```

(2) INFORMATION FOR SEQ ID NO: 5:

(i) SEQUENCE CHARACTERISTICS:
        (A) LENGTH: 1222 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION:8..700

(ix) FEATURE:

(A) NAME/KEY: mat_peptide
        (B) LOCATION:8..700

(xi) SEQUENCE DESCRIPTION: SEQ ID NO: 5:

```
TGCAGAG ATG AGT AAA CAA AGA GGA ACC TTC TCA GAA GTG AGT CTG GCC        49
        Met Ser Lys Gln Arg Gly Thr Phe Ser Glu Val Ser Leu Ala
        1               5                   10

CAG GAC CCA AAG CGG CAG CAA AGG AAA CCT AAA GGC AAT AAA AGC TCC        97
Gln Asp Pro Lys Arg Gln Gln Arg Lys Pro Lys Gly Asn Lys Ser Ser
15                  20                  25                  30

ATT TCA GGA ACC GAA CAG GAA ATA TTC CAA GTA GAA TTA AAT CTT CAA       145
Ile Ser Gly Thr Glu Gln Glu Ile Phe Gln Val Glu Leu Asn Leu Gln
                35                  40                  45

AAT CCT TCC CTG AAT CAT CAA GGG ATT GAT AAA ATA TAT GAC TGC CAA       193
Asn Pro Ser Leu Asn His Gln Gly Ile Asp Lys Ile Tyr Asp Cys Gln
            50                  55                  60

GGT TTA CTG CCA CCT CCA GAG AAG CTC ACT GCC GAG GTC CTA GGA ATC       241
Gly Leu Leu Pro Pro Pro Glu Lys Leu Thr Ala Glu Val Leu Gly Ile
        65                  70                  75

ATT TGC ATT GTC CTG ATG GCC ACT GTG TTA AAA ACA ATA GTT CTT ATT       289
Ile Cys Ile Val Leu Met Ala Thr Val Leu Lys Thr Ile Val Leu Ile
    80                  85                  90

CCT TTC CTG GAG CAG AAC AAT TCT TCC CCG AAT ACA AGA ACG CAG AAA       337
Pro Phe Leu Glu Gln Asn Asn Ser Ser Pro Asn Thr Arg Thr Gln Lys
95                  100                 105                 110

GCA CGT CAT TGT GGC CAT TGT CCT GAG GAG TGG ATT ACA TAT TCC AAC       385
Ala Arg His Cys Gly His Cys Pro Glu Glu Trp Ile Thr Tyr Ser Asn
                115                 120                 125

AGT TGT TAT TAC ATT GGT AAG GAA AGA AGA ACT TGG GAA GAG AGT TTG       433
Ser Cys Tyr Tyr Ile Gly Lys Glu Arg Arg Thr Trp Glu Glu Ser Leu
            130                 135                 140

CTG GCC TGT ACT TCG AAG AAC TCC AGT CTG CTT TCT ATA GAT AAT GAA       481
Leu Ala Cys Thr Ser Lys Asn Ser Ser Leu Leu Ser Ile Asp Asn Glu
        145                 150                 155

GAA GAA ATA AAA TTT CTG GCC AGC ATT TTA CCT TCC TCA TGG ATT GGT       529
Glu Glu Ile Lys Phe Leu Ala Ser Ile Leu Pro Ser Ser Trp Ile Gly
    160                 165                 170

GTG TTT CGT AAC AGC AGT CAT CAT CCA TGG GTG ACA ATA AAT GGT TTG       577
Val Phe Arg Asn Ser Ser His His Pro Trp Val Thr Ile Asn Gly Leu
175                 180                 185                 190

GCT TTC AAA CAT AAG ATA AAA GAC TCA GAT AAT GCT GAA CTT AAC TGT       625
Ala Phe Lys His Lys Ile Lys Asp Ser Asp Asn Ala Glu Leu Asn Cys
                195                 200                 205

GCA GTG CTA CAA GTA AAT CGA CTT AAA TCA GCC CAG TGT GGA TCT TCA       673
Ala Val Leu Gln Val Asn Arg Leu Lys Ser Ala Gln Cys Gly Ser Ser
            210                 215                 220

ATG ATA TAT CAT TGT AAG CAT AAG CTT TAGAAGTAAA GCATTTGCGT             720
Met Ile Tyr His Cys Lys His Lys Leu
        225                 230

TTACAGTGCA TCAGATACAT TTTATATTTC TTAAAATAGA AATATTATGA TTGCATAAAT     780

CTGAAAATGA ATTATGTTAT TGCTCTAAT ACAAAAATTC TAAATCAATT ATTGAAATAG      840

GATGCACACA ATTACTAAAG TACAGACATC CTAGCATTTG TGTCGGGCTC ATTTTGCTCA     900

ACATGGTATT TGTGGTTTTC AGCCTTTCTA AAAGTTGCAT GTTATGTGAG TCAGCTTATA     960

GGAAGTACCA AGAACAGTCA AACCCATGGA GACAGAAAGT AGAATAGTGG TTGCCAATGT    1020

CTCAGGGAGG TTGAAATAGG AGATGACCAC TAATTGATAG AACGTTTCTT TGTGTCGTGA    1080

TGAAAACTTT CTAAATTTCA GTAATGGTGA TGGTTGTAAC TTTGCAATA TACTAAACAT     1140
```

```
CATTGATTTT TAATCATTTT AAGTGCATGA AATGTATGCT TTGTACATGA CACTTCAATA      1200

AAGCTATCCA GAAAAAAAAA AA                                              1222
```

(2) INFORMATION FOR SEQ ID NO: 6:

(i) SEQUENCE CHARACTERISTICS:
        (A) LENGTH: 231 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ser Lys Gln Arg Gly Thr Phe Ser Glu Val Ser Leu Ala Gln Asp
 1               5                  10                  15

Pro Lys Arg Gln Gln Arg Lys Pro Lys Gly Asn Lys Ser Ser Ile Ser
                20                  25                  30

Gly Thr Glu Gln Glu Ile Phe Gln Val Glu Leu Asn Leu Gln Asn Pro
            35                  40                  45

Ser Leu Asn His Gln Gly Ile Asp Lys Ile Tyr Asp Cys Gln Gly Leu
        50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
                100                 105                 110

His Cys Gly His Cys Pro Glu Glu Trp Ile Thr Tyr Ser Asn Ser Cys
            115                 120                 125

Tyr Tyr Ile Gly Lys Glu Arg Arg Thr Trp Glu Glu Ser Leu Leu Ala
        130                 135                 140

Cys Thr Ser Lys Asn Ser Ser Leu Leu Ser Ile Asp Asn Glu Glu Glu
145                 150                 155                 160

Ile Lys Phe Leu Ala Ser Ile Leu Pro Ser Ser Trp Ile Gly Val Phe
                165                 170                 175

Arg Asn Ser Ser His His Pro Trp Val Thr Ile Asn Gly Leu Ala Phe
                180                 185                 190

Lys His Lys Ile Lys Asp Ser Asp Asn Ala Glu Leu Asn Cys Ala Val
            195                 200                 205

Leu Gln Val Asn Arg Leu Lys Ser Ala Gln Cys Gly Ser Ser Met Ile
        210                 215                 220

Tyr His Cys Lys His Lys Leu
225                 230
```

(2) INFORMATION FOR SEQ ID NO: 7:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 7:

```
CTGGAGCAGA ACAATTCTTC CCCGAATACA AGAACGCAGA AAGCACGTCA TTGTGGCCAT      60
```

-continued

```
TGTCCTGAGG AGTGGATTAC ATATTCCAAC AGTTGTTATT ACATTGGTAA GGAAAGAAGA      120

ACTTGGGAAG AGAGTTTGCT GGCCTGTACT TCGAAGAACT CCAGTCTGCT TTCTATAGAT      180

AATGAAGAAG AAATAAAATT TCTGGCCAGC ATTTTACCTT CCTCATGGAT TGGTGTGTTT      240

CGTAACAGCA GTCATCATCC ATGGGTGACA ATAAATGGTT TGGCTTTCAA ACATAAGATA      300

AAAGACTCAG ATAATGCTGA ACTTAACTGT GCAGTGCTAC AAGTAAATCG ACTTAAATCA      360

GCCCAGTGTG GATCTTCAAT GATATATCAT TGTAAGCATA AGCTT                      405
```

(2) INFORMATION FOR SEQ ID NO: 8:

(i) SEQUENCE CHARACTERISTICS:
        (A) LENGTH: 1755 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION:339..986

(ix) FEATURE:
        (A) NAME/KEY: mat_peptide
        (B) LOCATION:339..986

(xi) SEQUENCE DESCRIPTION: SEQ ID NO: 8:

```
GAGGAGTGGA TTACATATTC AACAGTTGT TATTACATTG GTAAGGAAAG AAGAACTTGG        60

GAAGAAAGAG TTTGCTGGCC TGTGCTTCGA AGAACTCTGA TCTGCTTTCT ATAGATAATG      120

AGGAAGAAAT GGTATGTGTG GGACTTCCC AGTTGGCTGT AAGTTGCCAT TTGAACTAAA       180

CGAAATAGAT CAGGAACTGA GGACATATCT AAATTTTCTA GTTTTATAGA AGGCTTTTAT      240

CCACAAGAAT CAAGATCTTC CCTCTCTGAG CAGGAATCCT TTGTGCATTG AAGACTTTAG      300

ATTCCTCTCT GCGGTAGACG TGCACTTATA AGTATTTG ATG GGG TGG ATT CGT          353
                                            Met Gly Trp Ile Arg
                                              1               5

GGT CGG AGG TCT CGA CAC AGC TGG GAG ATG AGT GAA TTT CAT AAT TAT        401
Gly Arg Arg Ser Arg His Ser Trp Glu Met Ser Glu Phe His Asn Tyr
             10                  15                  20

AAC TTG GAT CTG AAG AAG AGT GAT TTT TCA ACA CGA TGG CAA AAG CAA        449
Asn Leu Asp Leu Lys Lys Ser Asp Phe Ser Thr Arg Trp Gln Lys Gln
                 25                  30                  35

AGA TGT CCA GTA GTC AAA AGC AAA TGT AGA GAA AAT GCA TCT CCA TTT        497
Arg Cys Pro Val Val Lys Ser Lys Cys Arg Glu Asn Ala Ser Pro Phe
             40                  45                  50

TTT TTC TGC TGC TTC ATC GCT GTA GCC ATG GGA ATC CGT TTC ATT ATT        545
Phe Phe Cys Cys Phe Ile Ala Val Ala Met Gly Ile Arg Phe Ile Ile
     55                  60                  65

ATG GTA GCA ATA TGG AGT GCT GTA TTC CTA AAC TCA TTA TTC AAC CAA        593
Met Val Ala Ile Trp Ser Ala Val Phe Leu Asn Ser Leu Phe Asn Gln
 70                  75                  80                  85

GAA GTT CAA ATT CCC TTG ACC GAA AGT TAC TGT GGC CCA TGT CCT AAA        641
Glu Val Gln Ile Pro Leu Thr Glu Ser Tyr Cys Gly Pro Cys Pro Lys
                 90                  95                 100

AAC TGG ATA TGT TAC AAA AAT AAC TGC TAC CAA TTT TTT GAT GAG AGT        689
Asn Trp Ile Cys Tyr Lys Asn Asn Cys Tyr Gln Phe Phe Asp Glu Ser
            105                 110                 115
```

```
AAA AAC TGG TAT GAG AGC CAG GCT TCT TGT ATG TCT CAA AAT GCC AGC      737
Lys Asn Trp Tyr Glu Ser Gln Ala Ser Cys Met Ser Gln Asn Ala Ser
            120                 125                 130

CTT CTG AAA GTA TAC AGC AAA GAG GAC CAG GAT TTA CTT AAA CTG GTG      785
Leu Leu Lys Val Tyr Ser Lys Glu Asp Gln Asp Leu Leu Lys Leu Val
        135                 140                 145

AAG TCA TAT CAT TGG ATG GGA CTA GTA CAC ATT CCA ACA AAT GGA TCT      833
Lys Ser Tyr His Trp Met Gly Leu Val His Ile Pro Thr Asn Gly Ser
150                 155                 160                 165

TGG CAG TGG GAA GAT GGC TCC ATT CTC TCA CCC AAC CTA CTA ACA ATA      881
Trp Gln Trp Glu Asp Gly Ser Ile Leu Ser Pro Asn Leu Leu Thr Ile
                170                 175                 180

ATT GAA ATG CAG AAG GGA GAC TGT GCA CTC TAT GCC TCG AGC TTT AAA      929
Ile Glu Met Gln Lys Gly Asp Cys Ala Leu Tyr Ala Ser Ser Phe Lys
            185                 190                 195

GGC TAT ATA GAA AAC TGT TCA ACT CCA AAT ACA TAC ATC TGC ATG CAA      977
Gly Tyr Ile Glu Asn Cys Ser Thr Pro Asn Thr Tyr Ile Cys Met Gln
        200                 205                 210

AGG ACT GTG TAAAGATGAT CAACCATCTC AATAAAAGCC AGGAACAGAG             1026
Arg Thr Val
        215

AAGAGATTAC ACCAGCGGTA ACACTGCCAA CCGAGACTAA AGGAAACAAA CAAAAACAGG   1086

ACAAAATGAC CAAAGACTGT CAGATTTCTT AGACTCCACA GGACCAAACC ATAGAACAAT   1146

TTCACTGCAA ACATGCATGA TTCTCCAAGA CAAAAGAAGA GAGATCCTAA AGGCAATTCA   1206

GATATCCCCA AGGCTGCCTC TCCCACCACA AGCCCAGAGT GGATGGGCTG GGGGAGGGGT   1266

GCTGTTTTAA TTTCTAAAGG TAGGACCAAC ACCCAGGGGA TCACTGAAGG AAGAGAAGGC   1326

CAGCAGATCA GTGAGAGTGC AACCCCACCC TCCACAGGAA ATTGCCTCAT GGGCAGGGCC   1386

ACAGCAGAGA GACACAGCAT GGGCAGTGCC TTCCCTGCCT GTGGGGGTCA TGCTGCCACT   1446

TTTAATGGGT CCTCCACCCA ACGGGGTCAG GGAGGTGGTG CTGCCCCAGT GGGCCATGAT   1506

TATCTTAAAG GCATTATTCT CCAGCCTTAA GATCTTAGGA CGTTTCCTTT GCTATGATTT   1566

GTACTTGCTT GAGTCCCATG ACTGTTTCTC TTCCTCTCTT TCTTCCTTTT GGAATAGTAA   1626

TATCCATCCT ATGTTTGTCC CACTATTGTA TTTTGGAAGC ACATAACTTG TTTGGTTTCA   1686

CAGGTTCACA GTTAAGAAGG AATTTTGCCT CTGAATAAAT AGAATCTTGA GTCTCATGCA   1746

AAAAAAAAA                                                           1755

(2) INFORMATION FOR SEQ ID NO: 9:

(i) SEQUENCE CHARACTERISTICS:
        (A) LENGTH: 216 amino acids
        (B) TYPE: amino acid
        (D) TOPOLOGY: linear (ii) MOLECULE TYPE: protein (xi) SEQUENCE DESCRIPTION: SEQ ID NO: 9:

Met Gly Trp Ile Arg Gly Arg Arg Ser Arg His Ser Trp Glu Met Ser
1               5                   10                  15

Glu Phe His Asn Tyr Asn Leu Asp Leu Lys Lys Ser Asp Phe Ser Thr
                20                  25                  30

Arg Trp Gln Lys Gln Arg Cys Pro Val Val Lys Ser Lys Cys Arg Glu
            35                  40                  45

Asn Ala Ser Pro Phe Phe Phe Cys Cys Phe Ile Ala Val Ala Met Gly
        50                  55                  60
```

```
Ile Arg Phe Ile Ile Met Val Ala Ile Trp Ser Ala Val Phe Leu Asn
 65                  70                  75                  80

Ser Leu Phe Asn Gln Glu Val Gln Ile Pro Leu Thr Glu Ser Tyr Cys
                 85                  90                  95

Gly Pro Cys Pro Lys Asn Trp Ile Cys Tyr Lys Asn Asn Cys Tyr Gln
                100                 105                 110

Phe Phe Asp Glu Ser Lys Asn Trp Tyr Glu Ser Gln Ala Ser Cys Met
                115                 120                 125

Ser Gln Asn Ala Ser Leu Leu Lys Val Tyr Ser Lys Glu Asp Gln Asp
            130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
                180                 185                 190

Ala Ser Ser Phe Lys Gly Tyr Ile Glu Asn Cys Ser Thr Pro Asn Thr
            195                 200                 205

Tyr Ile Cys Met Gln Arg Thr Val
    210                 215

(2) INFORMATION FOR SEQ ID NO: 10:

(i) SEQUENCE CHARACTERISTICS:
        (A) LENGTH: 402 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 10:

TTCAACCAAG AAGTTCAAAT TCCCTTGACC GAAAGTTACT GTGGCCCATG TCCTAAAAAC      60

TGGATATGTT ACAAAAATAA CTGCTACCAA TTTTTTGATG AGAGTAAAAA CTGGTATGAG     120

AGCCAGGCTT CTTGTATGTC TCAAAATGCC AGCCTTCTGA AAGTATACAG CAAAGAGGAC     180

CAGGATTTAC TTAAACTGGT GAAGTCATAT CATTGGATGG GACTAGTACA CATTCCAACA     240

AATGGATCTT GGCAGTGGGA AGATGGCTCC ATTCTCTCAC CAACCTACT AACAATAATT      300

GAAATGCAGA AGGGAGACTG TGCACTCTAT GCCTCGAGCT TTAAAGGCTA TATAGAAAAC     360

TGTTCAACTC CAAATACATA CATCTGCATG CAAAGGACTG TG                       402

(2) INFORMATION FOR SEQ ID NO: 11:

(i) SEQUENCE CHARACTERISTICS:
        (A) LENGTH: 699 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 11:

ATGGATAACC AAGGAGTAAT CTACTCAGAC CTGAATCTGC CCCCAAACCC AAAGAGGCAG      60
```

```
CAACGAAAAC CTAAAGGCAA TAAAAGCTCC ATTTTAGCAA CTGAACAGGA AATAACCTAT      120

GCGGAATTAA ACCTTCAAAA AGCTTCTCAG GATTTTCAAG GGAATGACAA AACCTATCAC      180

TGCAAAGATT TACCATCAGC TCCAGAGAAG CTCATTGTTG GGATCCTGGG AATTATCTGT      240

CTTATCTTAA TGGCCTCTGT GGTAACGATA GTTGTTATTC CCTCTACATT AATACAGAGG      300

CACAACAATT CTTCCCTGAA TACAAGAACT CAGAAAGCAC GTCATTGTGG CCATTGTCCT      360

GAGGAGTGGA TTACATATTC CAACAGTTGT TACTACATTG GTAAGGAAAG AAGAACTTGG      420

GAAGAGAGTT TGCTGGCCTG TACTTCGAAG AACTCCAGTC TGCTTTCTAT AGATAATGAA      480

GAAGAAATGA AATTTCTGTC CATCATTTCA CCATCCTCAT GGATTGGTGT GTTTCGTAAC      540

AGCAGTCATC ATCCATGGGT GACAATGAAT GGTTTGGCTT TCAAACATGA GATAAAAGAC      600

TCAGATAATG CTGAACTTAA CTGTGCAGTG CTACAAGTAA ATCGACTTAA ATCAGCCCAG      660

TGTGGATCTT CAATAATATA TCATTGTAAG CATAAGCTT                             699

(2) INFORMATION FOR SEQ ID NO: 12:

(i) SEQUENCE CHARACTERISTICS:
        (A) LENGTH: 645 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 12:

ATGGATAACC AAGGAGTAAT CTACTCAGAC CTGAATCTGC CCCCAAACCC AAAGAGGCAG       60

CAACGAAAAC CTAAAGGCAA TAAAAGCTCC ATTTTAGCAA CTGAACAGGA AATAACCTAT      120

GCGGAATTAA ACCTTCAAAA AGCTTCTCAG GATTTTCAAG GGAATGACAA AACCTATCAC      180

TGCAAAGATT TACCATCAGC TCCAGAGAAG CTCATTGTTG GGATCCTGGG AATTATCTGT      240

CTTATCTTAA TGGCCTCTGT GGTAACGATA GTTGTTATTC CCTCACGTCA TTGTGGCCAT      300

TGTCCTGAGG AGTGGATTAC ATATTCCAAC AGTTGTTACT ACATTGGTAA GGAAAGAAGA      360

ACTTGGGAAG AGAGTTTGCT GGCCTGTACT TCGAAGAACT CCAGTCTGCT TTCTATAGAT      420

AATGAAGAAG AAATGAAATT TCTGTCCATC ATTTCACCAT CCTCATGGAT TGGTGTGTTT      480

CGTAACAGCA GTCATCATCC ATGGGTGACA ATGAATGGTT TGGCTTTCAA ACATGAGATA      540

AAAGACTCAG ATAATGCTGA ACTTAACTGT GCAGTGCTAC AAGTAAATCG ACTTAAATCA      600

GCCCAGTGTG GATCTTCAAT AATATATCAT TGTAAGCATA AGCTT                     645

(2) INFORMATION FOR SEQ ID NO: 13:

(i) SEQUENCE CHARACTERISTICS:
        (A) LENGTH: 693 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 13:
```

```
ATGAGTAAAC AAAGAGGAAC CTTCTCAGAA GTGAGTCTGG CCCAGGACCC AAAGCGGCAG    60

CAAAGGAAAC CTAAAGGCAA TAAAAGCTCC ATTTCAGGAA CCGAACAGGA AATATTCCAA   120

GTAGAATTAA ATCTTCAAAA TCCTTCCCTG AATCATCAAG GGATTGATAA AATATATGAC   180

TGCCAAGGTT TACTGCCACC TCCAGAGAAG CTCACTGCCG AGGTCCTAGG AATCATTTGC   240

ATTGTCCTGA TGGCCACTGT GTTAAAAACA ATAGTTCTTA TTCCTTTCCT GGAGCAGAAC   300

AATTCTTCCC CGAATACAAG AACGCAGAAA GCACGTCATT GTGGCCATTG TCCTGAGGAG   360

TGGATTACAT ATTCCAACAG TTGTTATTAC ATTGGTAAGG AAAGAAGAAC TTGGGAAGAG   420

AGTTTGCTGG CCTGTACTTC GAAGAACTCC AGTCTGCTTT CTATAGATAA TGAAGAAGAA   480

ATAAAATTTC TGGCCAGCAT TTTACCTTCC TCATGGATTG GTGTGTTTCG TAACAGCAGT   540

CATCATCCAT GGGTGACAAT AAATGGTTTG GCTTTCAAAC ATAAGATAAA AGACTCAGAT   600

AATGCTGAAC TTAACTGTGC AGTGCTACAA GTAAATCGAC TTAAATCAGC CCAGTGTGGA   660

TCTTCAATGA TATATCATTG TAAGCATAAG CTT                                693
```

(2) INFORMATION FOR SEQ ID NO: 14:

(i) SEQUENCE CHARACTERISTICS:
        (A) LENGTH: 648 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 14:

```
ATGGGGTGGA TTCGTGGTCG GAGGTCTCGA CACAGCTGGG AGATGAGTGA ATTTCATAAT    60

TATAACTTGG ATCTGAAGAA GAGTGATTTT TCAACACGAT GGCAAAAGCA AAGATGTCCA   120

GTAGTCAAAA GCAAATGTAG AGAAAATGCA CTCCCATTTT TTTTCTGCTG CTTCATCGCT   180

GTAGCCATGG GAATCCGTTT CATTATTATG GTAGCAATAT GGAGTGCTGT ATTCCTAAAC   240

TCATTATTCA ACCAAGAAGT TCAAATTCCC TTGACCGAAA GTTACTGTGG CCCATGTCCT   300

AAAAACTGGA TATGTTACAA AAATAACTGC TACCAATTTT TTGATGAGAG TAAAAACTGG   360

TATGAGAGCC AGGCTTCTTG TATGTCTCAA AATGCCAGCC TTCTGAAAGT ATACAGCAAA   420

GAGGACCAGG ATTTACTTAA ACTGGTGAAG TCATATCATT GGATGGGACT AGTACACATT   480

CCAACAAATG GATCTTGGCA GTGGGAAGAT GGCTCCATTC TCTCACCCAA CCTACTAACA   540

ATAATTGAAA TGCAGAAGGG AGACTGTGCA CTCTATGCCT CGAGCTTTAA AGGCTATATA   600

GAAAACTGTT CAACTCCAAA TACATACATC TGCATGCAAA GGACTGTG               648
```

(2) INFORMATION FOR SEQ ID NO: 15:

(i) SEQUENCE CHARACTERISTICS:
        (A) LENGTH: 1333 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:

(A) NAME/KEY: CDS
                (B) LOCATION:165..809

(ix) FEATURE:
                (A) NAME/KEY: mat_peptide
                (B) LOCATION:165..809

(xi) SEQUENCE DESCRIPTION: SEQ ID NO: 15:

```
GCAGGCATTG TTTGTTCTTG TCTTGGATTT ATGCCTTTAA ATTTCACCTT TTATTACACA        60

GCTATAGCAG GCCTTTTTAT GAGACTAACC TGGCCTCTCC ACTAAAGGAT GTGTGACTTT       120

CTGGGGACAG AAGAGTACAG TCCCTGACAT CACACACTGC AGAG ATG GAT AAC CAA       176
                                                Met Asp Asn Gln
                                                 1

GGA GTA ATC TAC TCA GAC CTG AAT CTG CCC CCA AAC CCA AAG AGG CAG        224
Gly Val Ile Tyr Ser Asp Leu Asn Leu Pro Pro Asn Pro Lys Arg Gln
  5              10                  15                  20

CAA CGA AAA CCT AAA GGC AAT AAA AGC TCC ATT TTA GCA ACT GAA CAG        272
Gln Arg Lys Pro Lys Gly Asn Lys Ser Ser Ile Leu Ala Thr Glu Gln
             25                  30                  35

GAA ATA ACC TAT GCG GAA TTA AAC CTT CAA AAA GCT TCT CAG GAT TTT        320
Glu Ile Thr Tyr Ala Glu Leu Asn Leu Gln Lys Ala Ser Gln Asp Phe
         40                  45                  50

CAA GGG AAT GAC AAA ACC TAT CAC TGC AAA GAT TTA CCA TCA GCT CCA        368
Gln Gly Asn Asp Lys Thr Tyr His Cys Lys Asp Leu Pro Ser Ala Pro
     55                  60                  65

GAG AAG CTC ATT GTT GGG ATC CTG GGA ATT ATC TGT CTT ATC TTA ATG        416
Glu Lys Leu Ile Val Gly Ile Leu Gly Ile Ile Cys Leu Ile Leu Met
 70                  75                  80

GCC TCT GTG GTA ACG ATA GTT GTT ATT CCC TCA CGT CAT TGT GGC CAT        464
Ala Ser Val Val Thr Ile Val Val Ile Pro Ser Arg His Cys Gly His
 85                  90                  95                 100

TGT CCT GAG GAG TGG ATT ACA TAT TCC AAC AGT TGT TAC TAC ATT GGT        512
Cys Pro Glu Glu Trp Ile Thr Tyr Ser Asn Ser Cys Tyr Tyr Ile Gly
                105                 110                 115

AAG GAA AGA AGA ACT TGG GAA GAG AGT TTG CTG GCC TGT ACT TCG AAG        560
Lys Glu Arg Arg Thr Trp Glu Glu Ser Leu Leu Ala Cys Thr Ser Lys
                120                 125                 130

AAC TCC AGT CTG CTT TCT ATA GAT AAT GAA GAA GAA ATG AAA TTT CTG        608
Asn Ser Ser Leu Leu Ser Ile Asp Asn Glu Glu Glu Met Lys Phe Leu
            135                 140                 145

TCC ATC ATT TCA CCA TCC TCA TGG ATT GGT GTG TTT CGT AAC AGC AGT        656
Ser Ile Ile Ser Pro Ser Ser Trp Ile Gly Val Phe Arg Asn Ser Ser
150                 155                 160

CAT CAT CCA TGG GTG ACA ATG AAT GGT TTG GCT TTC AAA CAT GAG ATA        704
His His Pro Trp Val Thr Met Asn Gly Leu Ala Phe Lys His Glu Ile
165                 170                 175                 180

AAA GAC TCA GAT AAT GCT GAA CTT AAC TGT GCA GTG CTA CAA GTA AAT        752
Lys Asp Ser Asp Asn Ala Glu Leu Asn Cys Ala Val Leu Gln Val Asn
                185                 190                 195

CGA CTT AAA TCA GCC CAG TGT GGA TCT TCA ATA ATA TAT CAT TGT AAG        800
Arg Leu Lys Ser Ala Gln Cys Gly Ser Ser Ile Ile Tyr His Cys Lys
                200                 205                 210

CAT AAG CTT TAGAGGTAAA GCGTTTGCAT TTGCAGTGCA TCAGATAAAT               849
His Lys Leu
        215

TGTATATTTC TTAAAATAGA AATATATTAT GATTGCATAA ATCTTAAAAT GAATTATGTT       909

ATTTGCTCTA ATAAGAAAAT TCTAAATCAA TTATTGAAAC AGGATACACA CAATTACTAA       969

AGTACAGACA TCCTAGCATT TGTGTCGGGC TCATTTTGCT CAACATGGTA TTTGTGGTTT      1029
```

```
TCAGCCTTTC TAAAAGTTGC ATGTTATGTG AGTCAGCTTA TAGGAAGTAC CAAGAACAGT   1089

CAAACCCATG GAGACAGAAA GTAGAATAGT GGTTGCCAAT GTCTGAGGGA GGTTGAAATA   1149

GGAGATGACC TCTAACTGAT AGAACGTTAC TTTGTGTCGT GATGAAAACT TTCTAAATTT   1209

CAGTAGTGGT GATGGTTGTA ACTCTGCGAA TATACTAAAC ATCATTGATT TTAATCATT   1269

TTAAGTGCAT GAAATGTATG CTTTGTACAC GACACTTCAA TAAAGCTATC CAGAAAAAAA   1329

AAAA                                                                1333
```

(2) INFORMATION FOR SEQ ID NO: 16:

(i) SEQUENCE CHARACTERISTICS:
        (A) LENGTH: 215 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Asp Asn Gln Gly Val Ile Tyr Ser Asp Leu Asn Leu Pro Pro Asn
 1               5                  10                  15

Pro Lys Arg Gln Gln Arg Lys Pro Lys Gly Asn Lys Ser Ser Ile Leu
                20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
        50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Ile Pro Ser Arg
                85                  90                  95

His Cys Gly His Cys Pro Glu Glu Trp Ile Thr Tyr Ser Asn Ser Cys
                100                 105                 110

Tyr Tyr Ile Gly Lys Glu Arg Arg Thr Trp Glu Glu Ser Leu Leu Ala
            115                 120                 125

Cys Thr Ser Lys Asn Ser Ser Leu Leu Ser Ile Asp Asn Glu Glu Glu
        130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
        195                 200                 205

Tyr His Cys Lys His Lys Leu
    210                 215
```

(2) INFORMATION FOR SEQ ID NO: 17:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 17:

```
Gln Arg His Asn Asn Ser Ser Leu Asn Thr Arg Thr Gln Lys Ala Arg
1               5                   10                  15
His Cys Gly His Cys Pro Glu Glu Trp Ile Thr Tyr Ser Asn Ser Cys
                20                  25                  30
Tyr Tyr Ile Gly Lys Glu Arg Arg Thr Trp Glu Glu Ser Leu Leu Ala
            35                  40                  45
Cys Thr Ser Lys Asn Ser Ser Leu Leu Ser Ile Asp Asn Glu Glu Glu
    50                  55                  60
Met Lys Phe Leu Ser Ile Ile Ser Pro Ser Ser Trp Ile Gly Val Phe
65                  70                  75                  80
Arg Asn Ser Ser His His Pro Trp Val Thr Met Asn Gly Leu Ala Phe
                85                  90                  95
Lys His Glu Ile Lys Asp Ser Asp Asn Ala Glu Leu Asn Cys Ala Val
                100                 105                 110
Leu Gln Val Asn Arg Leu Lys Ser Ala Gln Cys Gly Ser Ser Ile Ile
            115                 120                 125
Tyr His Cys Lys His Lys Leu
    130                 135
```

(2) INFORMATION FOR SEQ ID NO: 18:

(i) SEQUENCE CHARACTERISTICS:
    (A) LENGTH: 120 amino acids
    (B) TYPE: amino acid
    (C) STRANDEDNESS:
    (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 18:

```
Arg His Cys Gly His Cys Pro Glu Glu Trp Ile Thr Tyr Ser Asn Ser
1               5                   10                  15
Cys Tyr Tyr Ile Gly Lys Glu Arg Arg Thr Trp Glu Glu Ser Leu Leu
                20                  25                  30
Ala Cys Thr Ser Lys Asn Ser Ser Leu Leu Ser Ile Asp Asn Glu Glu
            35                  40                  45
Glu Met Lys Phe Leu Ser Ile Ile Ser Pro Ser Ser Trp Ile Gly Val
    50                  55                  60
Phe Arg Asn Ser Ser His His Pro Trp Val Thr Met Asn Gly Leu Ala
65                  70                  75                  80
Phe Lys His Glu Ile Lys Asp Ser Asp Asn Ala Glu Leu Asn Cys Ala
                85                  90                  95
Val Leu Gln Val Asn Arg Leu Lys Ser Ala Gln Cys Gly Ser Ser Ile
            100                 105                 110
Ile Tyr His Cys Lys His Lys Leu
            115                 120
```

(2) INFORMATION FOR SEQ ID NO: 19:

(i) SEQUENCE CHARACTERISTICS:
        (A) LENGTH: 135 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 19:

Leu Glu Gln Asn Asn Ser Ser Pro Asn Thr Arg Thr Gln Lys Ala Arg
1               5                   10                  15

His Cys Gly His Cys Pro Glu Glu Trp Ile Thr Tyr Ser Asn Ser Cys
            20                  25                  30

Tyr Tyr Ile Gly Lys Glu Arg Arg Thr Trp Glu Glu Ser Leu Leu Ala
        35                  40                  45

Cys Thr Ser Lys Asn Ser Ser Leu Leu Ser Ile Asp Asn Glu Glu Glu
    50                  55                  60

Ile Lys Phe Leu Ala Ser Ile Leu Pro Ser Ser Trp Ile Gly Val Phe
65                  70                  75                  80

Arg Asn Ser Ser His His Pro Trp Val Thr Ile Asn Gly Leu Ala Phe
                85                  90                  95

Lys His Lys Ile Lys Asp Ser Asp Asn Ala Glu Leu Asn Cys Ala Val
            100                 105                 110

Leu Gln Val Asn Arg Leu Lys Ser Ala Gln Cys Gly Ser Ser Met Ile
        115                 120                 125

Tyr His Cys Lys His Lys Leu
130                 135

(2) INFORMATION FOR SEQ ID NO: 20:

(i) SEQUENCE CHARACTERISTICS:
        (A) LENGTH: 134 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 20:

Phe Asn Gln Glu Val Gln Ile Pro Leu Thr Glu Ser Tyr Cys Gly Pro
1               5                   10                  15

Cys Pro Lys Asn Trp Ile Cys Tyr Lys Asn Asn Cys Tyr Gln Phe Phe
            20                  25                  30

Asp Glu Ser Lys Asn Trp Tyr Glu Ser Gln Ala Ser Cys Met Ser Gln
        35                  40                  45

Asn Ala Ser Leu Leu Lys Val Tyr Ser Lys Glu Asp Gln Asp Leu Leu
    50                  55                  60

Lys Leu Val Lys Ser Tyr His Trp Met Gly Leu Val His Ile Pro Thr
65                  70                  75                  80

Asn Gly Ser Trp Gln Trp Glu Asp Gly Ser Ile Leu Ser Pro Asn Leu
                85                  90                  95

```
Leu Thr Ile Ile Glu Met Gln Lys Gly Asp Cys Ala Leu Tyr Ala Ser
            100                 105                 110

Ser Phe Lys Gly Tyr Ile Glu Asn Cys Ser Thr Pro Asn Thr Tyr Ile
        115                 120                 125

Cys Met Gln Arg Thr Val
    130
```

(2) INFORMATION FOR SEQ ID NO: 21:

(i) SEQUENCE CHARACTERISTICS:
        (A) LENGTH: 233 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 21:

```
Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
            35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly
                165                 170                 175

Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
        195                 200                 205

Ala Val Leu Gln Val Asn Arg Leu Lys Ser Ala Gln Cys Gly Ser Ser
    210                 215                 220

Ile Ile Tyr His Cys Lys His Lys Leu
225                 230
```

(2) INFORMATION FOR SEQ ID NO: 22:

(i) SEQUENCE CHARACTERISTICS:
        (A) LENGTH: 215 amino acids (B) TYPE: amino acid
          (C) STRANDEDNESS:
          (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 22:

```
Met Asp Asn Gln Gly Val Ile Tyr Ser Asp Leu Asn Leu Pro Pro Asn
1               5                  10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Arg
                85                  90                  95

His Cys Gly His Cys Pro Glu Glu Trp Ile Thr Tyr Ser Asn Ser Cys
            100                 105                 110

Tyr Tyr Ile Gly Lys Glu Arg Arg Thr Trp Glu Glu Ser Leu Leu Ala
        115                 120                 125

Cys Thr Ser Lys Asn Ser Ser Leu Leu Ser Ile Asp Asn Glu Glu Glu
    130                 135                 140

Met Lys Phe Leu Ser Ile Ile Ser Pro Ser Ser Trp Ile Gly Val Phe
145                 150                 155                 160

Arg Asn Ser Ser His His Pro Trp Val Thr Met Asn Gly Leu Ala Phe
                165                 170                 175

Lys His Glu Ile Lys Asp Ser Asp Asn Ala Glu Leu Asn Cys Ala Val
            180                 185                 190

Leu Gln Val Asn Arg Leu Lys Ser Ala Gln Cys Gly Ser Ser Ile Ile
        195                 200                 205

Tyr His Cys Lys His Lys Leu
    210                 215
```

(2) INFORMATION FOR SEQ ID NO: 23:

(i) SEQUENCE CHARACTERISTICS:
          (A) LENGTH: 231 amino acids
          (B) TYPE: amino acid
          (C) STRANDEDNESS:
          (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 23:

```
Met Ser Lys Gln Arg Gly Thr Phe Ser Glu Val Ser Leu Ala Gln Asp
1               5                  10                  15

Pro Lys Arg Gln Gln Arg Lys Pro Lys Gly Asn Lys Ser Ser Ile Ser
```

-continued

```
                20                  25                  30
Gly Thr Glu Gln Glu Ile Phe Gln Val Glu Leu Asn Leu Gln Asn Pro
                35                  40                  45
Ser Leu Asn His Gln Gly Ile Asp Lys Ile Tyr Asp Cys Gln Gly Leu
    50                  55                  60
Leu Pro Pro Glu Lys Leu Thr Ala Glu Val Leu Gly Ile Ile Cys
65                  70                  75                  80
Ile Val Leu Met Ala Thr Val Leu Lys Thr Ile Val Leu Ile Pro Phe
                85                  90                  95
Leu Glu Gln Asn Asn Ser Ser Pro Asn Thr Arg Thr Gln Lys Ala Arg
                100                 105                 110
His Cys Gly His Cys Pro Glu Glu Trp Ile Thr Tyr Ser Asn Ser Cys
                115                 120                 125
Tyr Tyr Ile Gly Lys Glu Arg Arg Thr Trp Glu Glu Ser Leu Leu Ala
                130                 135                 140
Cys Thr Ser Lys Asn Ser Ser Leu Leu Ser Ile Asp Asn Glu Glu Glu
145                 150                 155                 160
Ile Lys Phe Leu Ala Ser Ile Leu Pro Ser Ser Trp Ile Gly Val Phe
                165                 170                 175
Arg Asn Ser Ser His His Pro Trp Val Thr Ile Asn Gly Leu Ala Phe
                180                 185                 190
Lys His Lys Ile Lys Asp Ser Asp Asn Ala Glu Leu Asn Cys Ala Val
                195                 200                 205
Leu Gln Val Asn Arg Leu Lys Ser Ala Gln Cys Gly Ser Ser Met Ile
    210                 215                 220
Tyr His Cys Lys His Lys Leu
225                 230
```

(2) INFORMATION FOR SEQ ID NO: 24:

(i) SEQUENCE CHARACTERISTICS:
        (A) LENGTH: 216 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: C-terminal (xi) SEQUENCE DESCRIPTION: SEQ ID NO: 24:

```
Met Gly Trp Ile Arg Gly Arg Ser Arg His Ser Trp Glu Met Ser
1               5                   10                  15
Glu Phe His Asn Tyr Asn Leu Asp Leu Lys Lys Ser Asp Phe Ser Thr
                20                  25                  30
Arg Trp Gln Lys Gln Arg Cys Pro Val Val Lys Ser Lys Cys Arg Glu
            35                  40                  45
Asn Ala Ser Pro Phe Phe Phe Cys Cys Phe Ile Ala Val Ala Met Gly
    50                  55                  60
Ile Arg Phe Ile Ile Met Val Ala Ile Trp Ser Ala Val Phe Leu Asn
65                  70                  75                  80
Ser Leu Phe Asn Gln Glu Val Gln Ile Pro Leu Thr Glu Ser Tyr Cys
                85                  90                  95
Gly Pro Cys Pro Lys Asn Trp Ile Cys Tyr Lys Asn Asn Cys Tyr Gln
```

```
                    100                 105                 110
Phe Phe Asp Glu Ser Lys Asn Trp Tyr Glu Ser Gln Ala Ser Cys Met
        115                 120                 125

Ser Gln Asn Ala Ser Leu Leu Lys Val Tyr Ser Lys Glu Asp Gln Asp
        130                 135                 140

Leu Leu Lys Leu Val Lys Ser Tyr His Trp Met Gly Leu Val His Ile
145                 150                 155                 160

Pro Thr Asn Gly Ser Trp Gln Trp Glu Asp Gly Ser Ile Leu Ser Pro
                165                 170                 175

Asn Leu Leu Thr Ile Ile Glu Met Gln Lys Gly Asp Cys Ala Leu Tyr
                180                 185                 190

Ala Ser Ser Phe Lys Gly Tyr Ile Glu Asn Cys Ser Thr Pro Asn Thr
        195                 200                 205

Tyr Ile Cys Met Gln Arg Thr Val
        210                 215
```

DNA AND AMINO ACID SEQUENCE SPECIFIC FOR NATURAL KILLER CELLS

This is a continuation of application Ser. No. 08/122,514, filed Sep. 24, 1993, (which is a 371 of PCT/US92/02469, filed Mar. 27, 1992) and now abandoned, which is a continuation-in-part of application Ser. No. 07/676,663, filed Mar. 28, 1991 and now abandoned.

This invention was made with partial government support under R 01 AI19007 awarded by the National Institutes of Health. The government has certain rights in the invention.

This invention relates to DNA and cDNA sequences which are normally transcribed in natural killer (NK) cells or in some T cells, vectors comprising the DNA or cDNA sequences and the proteins encoded by the DNA or cDNA sequences. The DNA sequences can be detected by employing a combination of differential hybridisation and cDNA subtraction methodology.

Natural killer (NK) cells are present in the peripheral blood in a state capable of lysing NK sensitive targets in a reaction that is not restricted by proteins of the major histocompatibility complex. These cells typically account for about 5% of peripheral blood lymphocytes and they usually possess the large granular lymphocyte (LGL) morphology. In human systems NK activity is usually defined as the ability to lyse cells of the promyeloid leukaemia, K562. In many cases stimulation of NK cells with interleukin 2 (IL-2) will confer on them lymphokine activated killer (LAK) activity, the ability to lyse a broader range of tumour target cells. Many ongoing studies are attempting to use cells with LAK activity in anti-tumour therapy.

From mRNA isolated from human NK cells it has been possible to generate a cDNA library from which has been isolated four related novel genes which constitute a new mammalian gene family, hereinafter designated NKG2. In sequence homology searches using standard selectivity criteria and the Intelligenetics software program to search the SwissProt and PIR databases, significant homologies were detected only with members of the type II transmembrane proteins with C-type animal lectin domains, and not with any other sequences. Although the overall sequence homology is low, they share homology throughout a stretch of approximately 120 amino acids with the most striking feature being the presence of six invariant cysteine residues at fixed positions. In the known transmembrane proteins, this region corresponds to a carbohydrate binding domain which enables the proteins to bind carbohydrates in a $Ca^{++}$ and pH-dependent manner (Drickamer 1988 J Biol Chem 263, 9557). It is therefore believed that the novel gene family of the present invention also codes for transmembrane proteins having a carbohydrate bonding domain.

The invention provides the genes coding for the extracellular part of four specific NKG2 transmembrane proteins, as well as for the complete transmembrane proteins. The invention also provides the corresponding proteins, hereinafter designated NKG2-A, -B, -C and -D.

A murine molecule belonging to the gene family of type II membrane proteins is described by Yokoyama (Yokoyama et al 1989 J. Immunol. 143). The murine Ly-49 alloantigen is recognised by the Al monoclonal antibody, and is a type II membrane protein, the expression of which is confined almost exclusively to a subset of mouse NK cells. The gene is found to map to the same position on mouse chromosome six as the gene for NK1.1, a commonly used murine NK cell marker also expressed almost exclusively on NK cells. Ly-49 is expressed on only about 20% of NK1.1 positive cells and is distinct from NK1.1.

A further molecule first identified by a special monoclonal antibody is described by Chambers (Chambers et al 1989 J Exp Med 169, 1373). This molecule corresponds to the antigen NKR-P1 and is expressed almost exclusively on rat NK cells. The reaction of this antibody with its target antigen delivers a transmembrane signal as evidenced by its ability to mediate reverse antibody-dependent cellular cytotoxicity of an appropriate Fc receptor positive target cell. The corresponding cDNA encodes a type II membrane protein of 223 amino acids (Giorda et al 1990 Science 249, 1298). Although the Ly-49 and NKR-P1 antigen genes have similarities with NKG2, they display very limited amino acid sequence homology, the homology with the NKG2-A protein sequence being 33% for Ly49 and 23% for NKRP1. It is accordingly most unlikely that NKG2 is simply the human equivalent of these murine genes (in which case an amino acid homology of approx. 70% or more would be expected), but rather represents a novel gene family.

The novel genes are preferentially expressed in NK cells and T cells of mammals, preferably of primates and most preferably of humans. By using a standard method such as Northern blot technique the mRNA corresponding to the genes of the invention can be detected in some T cells, but cannot be detected in B cells, on EBV-transformed B cell lines (EBV=Epstein-Barr virus) or other cells.

The present invention provides new DNA or cDNA sequences and novel proteins having the corresponding amino acid sequences, all of these being in isolated pure form. By "isolated pure form" is meant in a form substantially (>90%, preferably >95%) free of other DNA or protein of mammalian origin.

In particular, the invention provides an isolated DNA or cDNA molecule encoding the extracellular part of a transmembrane protein herein designated (a) NKG2-$A_f$, (b) NKG2-$B_f$, (c) NKG2-$C_f$ and (d) NKG2-$D_f$ (f=fragment) translated in natural killer cells or T cells, wherein the molecule contains a DNA or cDNA sequence selected from the group comprising:

a) that part of the DNA sequence shown in SEQ ID NO:1, comprising the nucleotides numbered 459 to 863 inclusive (=the entire sequence shown in SEQ ID NO:3); or b) that part of the DNA sequence shown in SEQ ID NO:1, comprising the nucleotides numbered 504 to 863 inclusive (=the entire sequence shown in SEQ ID NO:4); or c) that part of the DNA sequence shown in SEQ ID NO:5 comprising the nucleotides numbered 296 to 700 inclusive (=the entire sequence shown in SEQ ID NO:7); or d) that part of the DNA sequence shown in SEQ ID NO:8, comprising the nucleotides numbered 585 to 986 inclusive (=the entire sequence shown in SEQ ID NO: 10).

Additionally the invention comprises DNA or cDNA sequences that code for the same amino acid sequence as that coded for by any of a)–d) above; and/or which hybridise under stringent conditions to any of a)–d) above; and/or have a homology of 80 to 100% with any of the DNA sequences a)–d) above. A homology of 90 to 100% is preferred, more preferred is a homology of 95 to 100%, particularly preferred is 98 to 100%.

The activity of the extracellular part of the proteins comprises inter alia the recognition of a ligand on a cell surface, and there is evidence that said ligand is a carbohydrate structure which is for example expressed on cancer cells and virus infected cells (Drickamer 1988, J Biol Chem 263, 9557).

Additionally the invention provides an isolated DNA or cDNA molecule encoding a complete transmembrane protein herein designated aa) NKG2-A, bb) NKG2-B, cc)

NKG2-C and dd) NKG2-D which are translated in natural killer cells or T cells, wherein the molecule contains a DNA or cDNA sequence selected from the group comprising:

aa) that part of the DNA sequence shown in SEQ ID NO:1, comprising the nucleotides numbered 165 to 863 inclusive (=the entire sequence shown in SEQ ID NO:11), or bb) that part of the DNA sequence shown in SEQ ID NO:1, comprising the nucleotides numbered 165 to 863 inclusive; the nucleotides numbered 449 to 502 being deleted (=the entire sequence shown in SEQ ID NO:12); or cc) that part of the DNA sequence shown in SEQ ID NO:5 comprising the nucleotides numbered 8 to 700 inclusive (=the entire sequence shown in SEQ ID NO:13); or dd) that part of the DNA sequence shown in SEQ ID NO:8, comprising the nucleotides numbered 339 to 986 inclusive (=the entire sequence shown in SEQ ID NO: 14).

The deletion referred to in (bb) interrupts two codons, TC . . . T (Ser) and GC . . . A (Ala), but there is no effect upon the translation as the codon formed after the deletion, TCA, also codes for serine.

Additionally the invention comprises isolated DNA or cDNA sequences that code for the same amino acid sequence as that coded for by any of aa)–dd) above; and/or which hybridise under stringent conditions to any of aa)–dd) above; and/or have a homology of 80 to 100% with any of the DNA sequences aa)–dd) above. A homology of 90 to 100% is preferred, more preferred is a homology of 95 to 100%, particularly preferred is 98 to 100%.

The complete transmembrane protein is considered to be a receptor molecule the function of which comprises inter alia:

1) the recognition of a ligand on a cell surface, whereby said ligand may be a carbohydrate structure which is for example expressed on cancer cells and virus infected cells (but other structures are not excluded);

2) the transmission of a signal from the extracellular space into the cytoplasm;

3) the activation of NK or T cells by such signal resulting in the induction of cytotoxicity and/or proliferation.

Preferred DNA or cDNA sequences are those whose degree of homology with the reference DNA sequence are as given above, calculated on the basis of the total number of nucleotide changes in the coding region. Less preferred are those whose degree of homology is within the above ranges when calculated on the basis of only those nucleotide changes which give rise to a change in amino acid sequence.

The invention also includes DNA or cDNA sequences comprising the coding sequence from aa), bb), cc) or dd) and additionally a noncoding sequence. The complete sequences of the invention are shown in SEQ ID NOS:1,5,8 and 15. The given DNA sequences code for human proteins. Homologous DNA sequences coding for corresponding proteins found in other mammalian species are also preferred sequences.

A DNA sequence of the invention may be a cDNA recombinant DNA sequence which may be present in the genetic material of a host cell or non-human organism. The DNA of the invention can be transferred into prokaryotic or eucaryotic cells. The sequence of one of SEQ ID NOS:1,5,8 and 15 is combined with a suitable promoter such as tac-promoter and introduced into a suitable vector such as pGEX-2T or pKK233-2, which is then used to transform a prokaryotic cell such as E. coli (for example strain: Mo142).

The sequence of one of SEQ ID NOS:1,5,8 and 15 can also be directly introduced into a eukaryotic cell. Preferred cells are CHO cells or primate cells such as COS, because these latter cells guarantee the correct type of glycosylation. For optimum transcription in mammalian cells a suitable promoter has to be used with a compatible vector, for example CMV promoter in a pCDM8 vector.

The invention also provides the extracellular parts of the four transmembrane proteins encoded by the novel gene family, these extracellular parts being designated a') NKG2-$A_f$, b') NKG2-$B_f$, c') NKG2-$C_f$ and d') NKG2-$D_f$ (f=fragment) having amino acid sequences selected from the group comprising:

a') that part of the amino acid sequence in SEQ ID NOS:1 and 2 comprising the amino acids numbered 99 to 233 (=the entire amino acid sequence of SEQ ID NO:1); or b') that part of the amino acid sequence in SEQ ID NO:1 comprising the amino acids numbered 114 to 233 (=the entire amino acid sequence of SEQ ID NO:18); or c') that part of the amino acid sequence in SEQ ID NO:5 comprising the amino acids numbered 97 to 231 (=the entire amino acid sequence of SEQ ID NO:19); or d') that part of the amino acid sequence in SEQ ID NO:9 comprising the amino acids numbered 83 to 216 (=the entire amino acid sequence of SEQ ID NO:20).

Additionally the invention provides the isolated complete transmembrane proteins encoded by the novel gene family, designated aa') NKG2-A, bb') NKG2-B, cc') NKG2-C and dd') NKG2-D, having amino acid sequences selected from the group comprising:

aa') the amino acid sequence in SEQ ID NO:2 (or SEQ ID NO:21); pr bb') the amino acid sequence in SEQ ID NO:2 with the deletion of the amino acids numbered 96 to 113 (or SEQ ID NO:22); or cc') the amino acid sequence in SEQ ID NO:6 (or SEQ ID NO:23); or dd') the amino acid sequence in SEQ ID NO:8 (or SEQ ID NO:24).

Knowing the nucleotide sequences of the invention the person skilled in the art can synthesise the DNA according to the general procedure described in PCT Publication WO 90/07861. (Synthesis of oligonucleotides, amplification by the PCR reaction and splicing to from the complete. DNA sequence). Once the DNA sequence has been obtained it can be further amplified and introduced into a host cell for transcription and translation of the protein. The protein can be expressed, isolated and purified by standard methods.

The proteins of the invention show a considerable degree of similarity. The proteins each comprise an extracellular, a transmembrane and an intracellular segment. The transmembrane segments include the following amino acids: SEQ ID NO:2=from 71 to 98 inclusive or from 71 to 95 inclusive; SEQ ID NO:6=from 71 to 96 inclusive and SEQ ID NO:8= from 52 to 82 inclusive.

The protein NKG2-B (SEQ ID NO:1 including deletion or SEQ ID NO:15, ) is identical to NKG2-A (SEQ ID NO:1) except for the absence of an 18 amino acid segment immediately outside the transmembrane region. NKG2-C (SEQ ID NO:5) shows the strongest homology (94%) with the extracellular segment of NKG2-A and lesser homology (56%) throughout the intracellular and transmembrane segments, giving an overall homology of 76%. NKG2-D (SEQ ID NO:8) displays distant but significant homology (21%) with NKG2-A, NKG2-B and NKG2-C. FIG. 1 shows a diagram of the regions of homology in the DNA sequences of the transcripts. The shaded areas refer to the percent homology between the adjacent transcripts. The stippled region within the NKG2-A, NKG2-B and NKG2-C transcripts is 95% homologous with the 5' end of NKG2-D.

The proteins of the invention have similar functions to those of the known type II integral membrane proteins. The proteins deliver transmembrane signals. The extracellular C-terminus and the intracellular N-terminus are connected by a hydrophobic region capable of serving as a transmembrane domain. The extracellular segment can be activated by specific molecules, for example monoclonal antibodies specifically recognising the extracellular segment. By forming a complex between the inducing molecule and the protein of the invention the three dimensional structure of the protein of the invention is altered. The intracellular segment changes its configuration, the lytic activity is increased. When the protein of the invention is recognised by the inducing molecule the killer function is activated.

The present invention includes not only proteins having exactly the same amino acid sequence as those described above, but also proteins which are sequence variants of the above proteins. A "sequence variant" is defined herein as a protein which has a homology of at least 70%, preferably at least 80%, more preferably at least 90%, particularly at least 95%, with one of the proteins a')–d'); or a homology of at least 80%, preferably at least 90%, more preferably at least 95%, with one of the proteins aa')–dd'); and essentially the same biological properties as one of the proteins a')–d') or aa')–dd').

By "essentially the same biological properties" is meant that the sequence variant protein corresponding to the extracellular domain of the transmembrane protein or to the complete transmembrane protein must be capable of binding to a ligand molecule on an NK target cell, and that the complete transmembrane protein must be capable of transmitting a signal across the membrane.

Amino acid sequence variants of the inventive proteins include, for example, deletions from, or insertions or substitutions of, residues within the unmodified amino acid sequences. Any combination of deletion, insertion and substitution may also be made to arrive at the final construct, provided that the final construct possesses the desired activity. Obviously, any mutations made in the DNA encoding the variants must not place the sequence out of reading frame.

Amino acid sequence deletions generally range from about 1 to 30 residues, more preferably 1 to 10 residues, and typically are contiguous. Amino acid sequence insertions include amino- and/or carboxy-terminal fusions of from one residue to polypeptides of essentially unrestricted length, as well as intrasequence insertions of single or multiple amino acid residues. Intrasequence insertions may range generally from about 1 to 10 residues, more preferably 1 to 5.

The proteins of the invention very often consist of sequences with at least one altered amino acid residue compared with the amino acid sequence of the Sequence Identifier (referring to the amino acids) of the invention. Preferably only one has been removed and a different residue inserted in its place. Such substitutions generally are made in accordance with the following Table I when it is desired to modulate finely the characteristics of the proteins of the invention.

Substantial changes in function are made by selecting substitutions that are less conservative than those in Table I, i.e., selecting residues that differ more significantly in their effect on maintaining (a) the structure of the polypeptide backbone in the area of the substitution, for example, as a sheet or helical conformation, (b) the charge or hydrophobicity of the molecule at the receptor binding site, or (c) the bulk of the side chain.

TABLE I

| Original Residues | Exemplary Substitutions |
|---|---|
| Ala | Gly, Ser |
| Arg | Lys |
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

Most deletions and insertions, and substitutions in particular, are not expected to produce radical changes in the characteristics of the proteins of the inventions. However, it is difficult to predict the exact effect of the substitution, deletion or insertion in advance of doing so, for example, when modifying the receptor binding domain.

As the NKG2 proteins act as transmembrane proteins whose function it is to transmit a signal to activate the NK cell, it is believed that the NK immune response will be strengthened if the number of NKG2 protein molecules on the surface of the NK cell is increased.

In order to increase the number of expressed NKG2 molecules, the natural killer cells of patients suffering from cancer or viral disease may be isolated and transformed by the DNA of the invention. NK cells are obtainable from the blood, lymph node or spleen cells of a patient, and these cells may be transformed in vitro and re-injected into the patient. The isolated DNA sequence is introduced into patient-derived NK cells using known techniques of transfection for example by retroviral vectors. The protein encoded by such introduced DNA does not differ from person to person, unlike many other cell proteins (Major Histocompatibility Complex Antigen). Therefore an uncontrolled attack of the transformed cells against self antigens is excluded and the transformed cells themselves will not be attacked by the immune system.

The proteins of the invention may be obtained as the products of recombinant expression, using essentially standard methods, as outlined above and described in more detail below. The protein may be purified for example by the use of a polyclonal or monoclonal antibody which has been raised against a specific peptide sequence characteristic of the protein which it is desired to isolate.

The isolated proteins of the invention, preferably the extracellular domains, are useful as a diagnostic tool for detecting target ligands, for example carbohydrate groups which are present on cancer cells and some virus infected cells.

The isolated complete transmembrane protein is a suitable tool for the study of the mechanism of NK cell regulation. Additionally the natural three dimensional structure of the protein, which is part of a synthetic or natural membrane, makes it possible to test different chemical compounds which have an influence on the change of configuration to block or to enhance the triggering of the function of the transmembrane protein.

Additionally the proteins of the invention, preferably the extra-cellular parts of the proteins, may be linked to a cytotoxic molecule, for example ricin, to form a chimeric protein molecule capable of lysis of cancer and virus infected cells.

The purified proteins of the invention are also useful as antigens to produce monoclonal or polyclonal antibodies against the proteins, using standard methods which are well known to the person skilled in the art. Alternatively, instead of immunising animals such as mice with the purified antigen, cells bearing the protein molecules on the membrane may be used as immunogen. Using these methods antibodies are established against epitopes of the protein, the extracellular epitopes being preferred. The protein may be offered as an antigen on cells of a different species (e.g. human protein on murine syngeneic cells) to enrich the specific B cell population producing antibodies against the antigen. The murine cells are transformed by introducing the coding part of the human DNA of the invention preferably combined with a suitable promoter into the genetic material of the mouse cell. Then the transformed cells are injected into a syngeneic mouse as a highly specific immunogen. After producing hybridomas by fusion according to standard methods the monoclonal antibodies produced by the hybridomas are screened for example by ELISA with original (human) NK cells or with pure protein.

Further a monoclonal antibody or domain specifically recognising the proteins of the invention may be combined with a second monoclonal antibody or binding domain recognising a specific structure on cancer cells or virus-infected cells. A binding domain is part of at least one protein which recognises parts (for example epitopes) of the protein of the invention. A typical binding domain is the variable region of the heavy or light chain of an antibody. Such combined molecules or binding domains are useful for the treatment of specific forms of cancer. The production of bifunctional antibodies is described for example in J. Van Dijk et al (1989) Int J of Cancer 44:738–743.

In particular, the α-NKG2-mAbs or αNKG2-α-cancer-mAb-complexes cause an increase in the activity of human natural killer cells against human tumor cells, as shown in the $^{51}$[Cr] release test described by Brunner et al. (1981) J Exp Med 154: 362–373. Tumor cells as target cells which are labelled by $^{51}$[Cr] are incubated in the presence of NK cells for 4 to 6 hours. The effectiveness of the NK cells is measured by the release of $^{51}$[Cr] label into the medium. The $^{51}$[Cr] release is increased in the presence of the antibody or antibody complex according to the invention. Activity against gibbon tumour cells are tested in the same in vitro system with the exception that gibbon NK cells are used.

The free extracellular proteins of the invention, i.e. proteins aa')–dd'), are useful agents for blocking the ligand molecules on the NK target cells and are therefore useful as immunosuppressants in situations such as organ transplantation and autoimmune disease.

For these indications the appropriate dosage varies depending upon, for example, the host, the mode of administration and the nature and severity of the condition being treated. In general, satisfactory results in animals are obtained at daily dosages from about 20 μg to about 15 mg, preferably from 150 μg to 2 mg, per kg body weight. The dosages are administered in a single dose or in divided dosages up to four times per day.

The compounds of the invention are administered by any conventional route, in particular by injection in solution or suspension in a pharmaceutically acceptable diluent or carrier. Such compositions are manufactured in conventional manner.

EXAMPLES

Cell Culture

Figure 1:
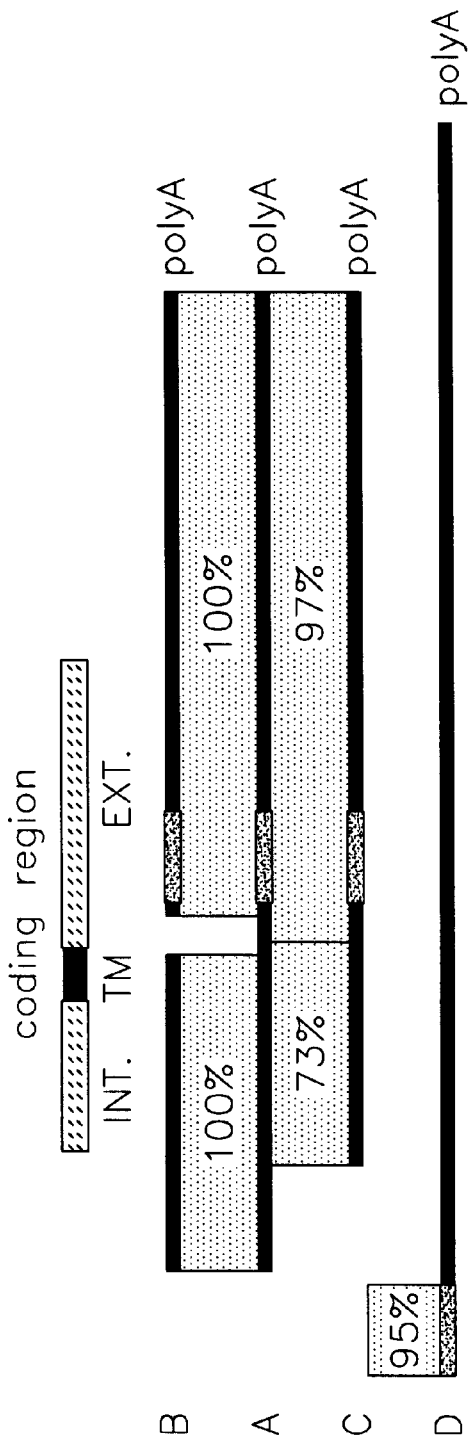
FIG. 1 shows a diagram of the regions of homology in the DNA sequences of the proteins of the invention, namely NKG2-A, NKG2-B, NKG2-C and NKG2-D. The shaded areas refer to the percent homology between the adjacent transcripted mRNAs. The stippled region within the NKG2-A, NKG2-B and NKG2-C transcripts is 95% homologous with the 5' end of NKG2-D. Above the four lines representing the mRNAs a translated protein is shown comprising the extracellular, the transmembrane and the intracellular part of the molecule.

The cloned human NK cell, B22 (CD3-, CD16-, CD56+), and the NK cell populations EDF (CD3-, CD16+, CD56-) and 221707 (CD3-, CD16+, CD56+) derived from NK cell leukocytosis patients are cultured in RPMI 1640 medium containing 15% pooled human serum, 20% T cell growth factor (TCGF) (Biotest, FRG), 2 mM L-glutamine, supplemented with streptomycin and penicillin. The cells are stimulated weekly with irradiated (10,000 Rad) LCL feeder cells (LCL=Lymphoblastoid cell line).

Cells are harvested and RNA isolated on day 6 or 7 of the growth cycle. Frozen PBL (=peripheral blood lymphocytes) from the patients are depleted for CD3+ cells (which constitute less than 15% of the original samples) by treatment with OKT3 and rabbit complement. The EDF culture is treated with LCL feeder cells at two week intervals and cells are harvested after 3 weeks of culture. 221707 is not treated with feeder cells and is harvested after 2 weeks of culture. After complement depletion of CD3+ cells and growth for 2 to 3 weeks in TCGF-containing medium, virtually 100% of the cells in the population have the NK phenotype. Allogeneic cytotoxic T cell clones (Tc) are cultured in the same medium as the NK cell lines and are stimulated weekly with LCL feeder cells. Tc1 and Tc2 are CD4+ and Tc3 is CD8+. The lymphoblastoid cell line, FJO, and the leukaemic T cell line, Jurkat, are cultured in RPMI 1640 containing 10% fetal calf serum, glutamine and antibiotics.

The CD4-positive allogeneic T cell clones, KD15, 0.3–78, KD33, and a CD4-positive cytomegalovirus-specific helper T cell clone, WRC-16, are cultured in the same medium as the NK clone. The chronic myelogenous leukaemia line, K562, the histocytic lymphoma line, U937, the Jurkat cell line, and FJO cell line are cultured in RPMI 1640 containing 10% fetal calf serum, glutamine and antibiotics. The T cell lymphoma line, Hut78, is cultured in the same medium as above, with the addition of 10% TCGF. The promyelocytic leukaemia line, HL60, is cultured in the same medium as above except that it contains 20% fetal calf serum. One half of the HL60 is stimulated with 1.25% DMSO at days 1 and 3 and harvested at day 7. DMSO (dimethyl sulfoxide) stimulation induces approximately 50% of the cells to differentiate into more mature myeloid cell forms. The monocyte line, THP-1, is cultured in RPMI 1640 containing 10% fetal calf serum and $2 \times 10^{-5}$M β-mercaptoethanol.

NK Cell Activation

B22, normally maintained in 20% TCGF, is resuspended in medium containing 5% TCGF, in which cells remain viable but do not proliferate. After two days, the cells are returned to medium containing 20% TCGF. Total cytoplasmic RNA is extracted at various time points and subjected to Northern blot analysis.

Isolation and Sequencing of NKG2 cDNA Clones 12 independent cDNA clones are isolated from the B22 cDNA library using differential hybridisation as described in the following.

cDNA Library Preparation

Messenger RNA used for preparation of cDNA libraries, Northern blots, or cDNA probe is extracted and eluted from oligo dT cellulose using the method of JE Badley et al. (1988): BioTechniques 6, 114. cDNA libraries of B22 and FJ0 are prepared using the method of Palazzolo & Meyerowitz (1987): Gene 52, 197. Briefly, 2 $\mu$g poly(A) RNA is converted to double-stranded cDNA using the Bethesda Research Laboratories cDNA Synthesis System, except that first-strand synthesis is primed with an oligonucleotide having an XbaI cloning site at its 5' end and a homopolymeric T tail at its 3' end. The double-stranded cDNA is methylated with EcoRI methylase, ligated to EcoRI linkers, and digested with EcoRI and XbaI. The cDNA is then size fractionated on a Biogel A50M column and all fractions with a minimum size of 400 bp are combined, ligated to EcoRI-XbaI arms of the Lambda ($\lambda$) GEM-2 vector (Promega Biotech), and packaged using Gigapack Gold (Stratagene). A library of $10^6$ primary plaques is amplified. The final libraries consist of cDNA inserts with an XbaI site adjacent to an SP6 RNA polymerase promoter at the 3' end of the message and an EcoRI site next to a T7 RNA polymerase promoter at the 5' end.

$\lambda$-DNA from libraries or clones is prepared from plate lysates using the polyethylene glycol/NaCl precipitation method described by T Maniatis et al. (1982) Cold Spring Harbor Laboratory, Cold Spring Harbor, N.Y. DNA preparations from the B22 and FJ0 libraries are subsequently used to prepare a subtracted cDNA library following the method of MJ Palazzolo et al. (1989): Neurone 3, 527. After digestion of library DNA with XbaI, T7 RNA polymerase is used to synthesise poly(A) RNA (hereafter referred to as synthetic RNA) which is immediately loaded onto an oligo (dT) cellulose column, and bound fractions containing approximately 80% of the newly synthesised RNA are recovered.

$^{32}$[P]-labelled first-strand cDNA is prepared from the B22 synthetic RNA using the same priming oligomer described above, and the RNA is subsequently base hydrolyzed. The annealing procedure and subsequent steps are carried out twice starting either with 2 or 6 $\mu$g of B22 first-strand cDNA. The cDNA is twice annealed to a 10–20 fold excess of FJ0 synthetic RNA at 42° for 72 hours in the presence of 40% formamide, 0.5 M sodium phosphate (pH 6.8), 10 mM EDTA and 0.2% SDS (sodium dodecylsulfate). After each annealing, the sample is applied to a BioRad HPHT HPLC column equilibrated with 10 mM sodium phosphate (pH 6.8) at 60°. Non-annealed, single-stranded cDNA is eluted with 154 mM phosphate buffer, and fractions containing cDNA are combined. After two cycles of subtraction approximately 0.2 $\mu$g single-stranded NK cDNA is recovered. An oligonucleotide homologous to a short vector encoded stretch at the 3' end of the subtracted first-strand cDNA is used to prime second-strand synthesis. The double-stranded cDNA is then cleaved with EcoRI and XbaI, size fractionated on a Biogel A50M column and ligated into EcoRI-XbaI $\lambda$GEM-2 arms. A total of 1100 plaques are obtained from the two trials after in vitro packaging and plating. Each plaque is picked with a glass capillary tube and the plug transferred to a well of a 96-well plate containing 100 $\mu$l of SM buffer.

Plaque Hybridisation Studies

Differential hybridisation is performed on plaque lifts prepared on nitro-cellulose membranes. During the first differential screening of the total library, lifts are prepared from 150 mm plates containing 500–800 plaques. All subsequent screenings are performed on ordered plaques prepared using a sterile stainless steel transfer device that duplicates the ordered array of a 96-well plate. First strand $^{32}$[P]-labelled cDNA probe is prepared from mRNA using the same conditions of cDNA synthesis described above except that dCTP is present at 25 $\mu$M and ($\alpha$-$^{32}$[P])dCTP is present at 3.5 $\mu$Ci/$\mu$l. RNA is base hydrolyzed and cDNA is separated from unincorporated label on a small Sephadex G50 column. Previously described gene probes are labelled using either the Nick Translation Kit or the Multiprime Labelling System from Amersham. Probes prepared from individual clones for cross-hybridization studies are of several types. In some cases, DNA inserts are excised from individual clones, electrophoresed on a 1.3% low melting point agarose gel and the insert band recovered from the gel and labelled using the multiprime labelling system of Amersham. Alternatively, one ng of $\lambda$-DNA from a clone is amplified by PCR using the GeneAmp system from Perkin Elmer Cetus. The amplified product is again purified on a 1.3% low melting point agarose gel and labelled using the Multiprime system. Plaque hybridisations with all DNA probes are carried out as in Maniatis et al. (Gyllenstein, U. B. & Erlich, H. A. (1988) Proc Natl Acad Sci USA 85, 7652). Asymmetric PCR is used to amplify inserts and the 5'-end sequence (up to 450 nucleotides in length) is determined for seven of the clones. A full length cDNA sequence is determined by subcloning PstI fragments encompassing the entire NKG2 insert into M13mp19.

NKG2 cDNA Probes

The NKG2 cDNA fragments are labelled using the multiprime system from Amersham. Labelled NKG2 cDNA fragments are used as probes in Northern blot hybridisation and plaque hybridisation.

Northern Blot Studies

RNA samples are isolated as described above. At appropriate time points after exposure to 20% TCGF, cells are lysed with a low concentration of NP40, nuclei are pelleted and the aqueous phase is extracted with phenol/chloroform. Northern analysis is performed as described by P Thomas (1980) Proc. Natl. Acad. Sci. USA 77, 5201. Briefly, RNA samples are denatured and applied to formaldehyde-agarose denaturing gels. The RNA is transferred from the gel to GeneScreen Plus (DuPont) by capillary blotting. Blots are prehybridised (1M NaCl, 50% formamide, 10% dextran sulphate, 5×Denhardts and 1% SDS) for 12–16 hours at 42° C. Labelled denatured DNA probe is added to the blot at 1×$10^6$ cpm/ml (cpm=counts per minute) hybridisation buffer, and hybridisation continued for 24 hours at 42° C. The blots are then washed and exposed for autoradiography.

Labelled NKG2 cDNA probes are mixed with denatured salmon sperm DNA (35 $\mu$g/ml hybridisation solution) and then added to the blot at 1–5×$10^6$ cpm/ml hybridisation buffer. Following overnight hybridisation at 42° C., blots are washed two times in 2×SSC for 5 min. at room temperature, then twice in 2×SSC and 1% SDS for 30 min. at 50° C.

Southern Blot Hybridisation

Genomic DNA is digested with the indicated restriction enzyme and 10 μg/lane of digested DNA is electrophoresed on a 0.7% agarose gel. The DNA is transferred to nitrocellulose membrane by capillary blotting using 20×SSC. Hybridisation and washes are performed as in Nicklas, J. A., et al. (1985) Human Immunol. 13, 95.

DNA Sequencing

Polymerase chain reaction amplifications used to prepare single-stranded DNA (Gyllensten & Erlich) for sequencing contain in 100 μl final volume: 1 ng λ-DNA, 50 mM Tris/HCl pH 8.8, 10 mM $MgCl_2$, 10 mM $(NH_4)_2SO_4$, 1.5 mM of each dNTP (=deoxynucleotide-triphosphate), 100 moles of SP6 polymerase promoter primer, 1 pmole T7 polymerase promoter primer (both from Promega), and 2.5 units Taq polymerase (Perkin Elmer Cetus). Samples are cycled 35 times through 1 min. denaturation at 94° C., 2 min. annealing at 49° C,, and 3 min. extension at 72° C. Following the amplification, samples are purified using Millipore Ultrafree-MC low binding filter units (10,000 mol weight cut-off). Approximately one-half of the amplified sample is then used for DNA sequencing which is carried out with standard protocols for Sequenase (USB) or Taq Track (Promega) if secondary structural problems are apparent. DNA sequences up to 450 nucleotides in length are obtained by this method. DNA sequence comparison with GenBank and EMBL databases is performed with the Intelligenetics FastDB program.

Formation of Antibodies to the Protein

Peptides are synthesised corresponding to a) the 15 C-terminal amino acids of NKG2-C and b) the 15 amino acids of position 157–171 of NKG2-C. This latter sequence forms part of the lectin domain, and is predicted to constitute surface exposed helices. Both peptides are synthesised with an additional cysteine on their N-terminus, conjugated to KLH and used for immunization of several rabbits according to standard procedures. Antibodies raised against the peptides are purified from the rabbit sera via a peptide column.

Production of Recombinant Protein

Expression of Complete Protein in Insect Cells

Recombinant NKG2-C protein is produced in the baculovirus system according to published procedures (Invitrogen Manual). The NKG2-C cDNA is cloned into the pVL1393 baculovirus expression vector and Sf9 insect cells are cotransfected with the plasmid and wild type viral DNA. Recombinant virus, which contains the NKG2-C DNA integrated into the viral genome by homologous recombination of the plasmid with the wild type viral DNA, is selected by four rounds of plaque purification. Recombinant virus is scored on filter replicas obtained from infected cells. Following purification of the recombinant virus from wild type viruses, infections of Sf9 cells are performed at different virus to cell ratios. The production of recombinant NKG2-C protein is determined after lysis of the infected cells in buffers containing 1% Triton®X-100. Identical amounts of protein are separated on polyacrylamide gels, the proteins electrophoretically transferred to Immobilion-P membranes and NKG2-C detected by its reactivity in Western blots with the polyclonal anti-peptide antibodies. No product is detected in this way in controls infected only with wild type virus. The estimated molecular weight in PAGE is consistent with the predicted value of 26 kD.

Expression of Extracellular Domain in E coli

The cDNA for NKG2-C is cut with the BstNI restriction endonuclease at the start of the region encoding the extracellular domain, and the fragment cloned into the EcoRI site of the pFlag1 plasmid. This construct directs the secretion of a flag-NKG2-C fusion protein to the periplasmic space with the help of the ompA signal peptide. The flag is an eight amino acid tag-sequence added for the purpose of easier purification only. Extracts from E coli obtained after osmotic shock of the cells is used for protein transfer blots with the antibodies described above. A protein of approx. 17 kD reactive with the antibody is found in the extract from the transfected E coli but not in control extracts obtained from parallel cultures transfected with the expression vector without a NKG2-C insert.

Purification of Recombinant Protein

Crude protein isolated by lysis of Sf9 cells from a large-scale fermentation of transfected cells is purified on an immunoaffinity column the stationary phase of which is bonded to one of the two anti-NKG2-C peptide antibodies described above. The column is then eluted at pH 3–4 to remove the desired protein from the column, and the protein is further purified using standard techniques for example ion-exchange and reverse-phase chromatography. The purity of the product can be estimated by SDS-PAGE.

Crude protein from fermentation of E coli is purified in similar manner using on the immunoaffinity column a commercially available MAb to the flag peptide. The eluted protein is specifically cleaved from the flag peptide by enterokinase, and purified by conventional methods.

---

We claim:

1. An isolated DNA encoding the transmembrane protein NKG2-A, NKG2-B, NKG2-C or NKG2-D, said DNA being an isolated DNA that codes for the amino acid sequence of SEQ ID NO:21, 22, 23 or 24.

2. An isolated DNA according to claim 1 that codes for the amino acid sequence of SEQ ID NO:21.

3. An isolated DNA according to claim 1 that codes for the amino acid sequence of SEQ ID NO:22.

4. An isolated DNA according to claim 1 that codes for the amino acid sequence of SEQ ID NO:23.

5. An isolated DNA according to claim 1 that codes for the amino acid sequence of SEQ ID NO:24.

6. An isolated DNA according to claim 1 selected from the group consisting of
    (a) the isolated DNA of SEQ ID NO:11,
    (b) the isolated DNA of SEQ ID NO:12,
    (c) the isolated DNA of SEQ ID NO:13 and
    (d) the isolated DNA of SEQ ID NO:14.

7. An isolated DNA encoding the extracellular domain of the transmembrane protein NKG2-A, NKG2-B, NKG2-C or NKG2-D, said DNA being an isolated DNA that codes for the amino acid sequence of (i) SEQ ID NO:17, (ii) SEQ ID NO:18, (iii) SEQ ID NO:19 or (iv) SEQ ID NO:20.

8. An isolated DNA according to claim 7 selected from the group consisting of
    (a) the isolated DNA of SEQ ID NO:3,
    (b) the isolated DNA of SEQ ID NO:4,
    (c) the isolated DNA of SEQ ID NO:7 and
    (d) the isolated DNA of SEQ ID NO:10.

9. An isolated protein which is the transmembrane protein NKG2-A, NKG2-B, NKG2-C or NKG2-D and having an amino acid sequence selected from the group consisting of
    (a) the amino acid sequence of SEQ ID NO:21,
    (b) the amino acid sequence of SEQ ID NO:22,
    (c) the amino acid sequence of SEQ ID NO:23 and
    (d) the amino acid sequence of SEQ ID NO:24.

10. An isolated protein according to claim 9 having the amino acid sequence of SEQ ID NO:21.

11. An isolated protein according to claim 9 having the amino acid sequence of SEQ ID NO:22.

12. An isolated protein according to claim 9 having the amino acid sequence of SEQ ID NO:24.

13. An isolated protein which is the extracellular domain of the transmembrane protein NKG2-A, NKG2-B, NKG2-C or NKG2-D, said protein having an amino acid sequence selected from the group consisting of
    (a) the amino acid sequence of SEQ ID NO:17,
    (b) the amino acid sequence of SEQ ID NO:18,
    (c) the amino acid sequence of SEQ ID NO:19 and
    (d) the amino acid sequence of SEQ ID NO:20.

14. A chimeric protein comprising a cytotoxic protein linked to a protein which is the extracellular domain of the transmembrane protein NKG2-A, NKG2-B, NKG2-C or NKG2-D, said extracellular domain having an amino acid sequence selected from the group consisting of
    (a) the amino acid sequence of SEQ ID NO:17,
    (b) the amino acid sequence of SEQ ID NO:18,
    (c) the amino acid sequence of SEQ ID NO:19 and
    (d) the amino acid sequence of SEQ ID NO:20.

15. A method of treating a viral infection comprising administering to a human having a viral infection an effective amount of a chimeric protein according to claim 14, said effective amount being an amount effective for the treatment of a viral infection.

16. A method of treating cancer comprising administering to a human having cancer an effective amount of a chimeric protein according to claim 14, said effective amount being an amount effective for the treatment of cancer.

* * * * *